April 16, 1963 C. FISCHER Plant Pat. 2,253
GLADIOLUS PLANT
Filed May 9, 1962
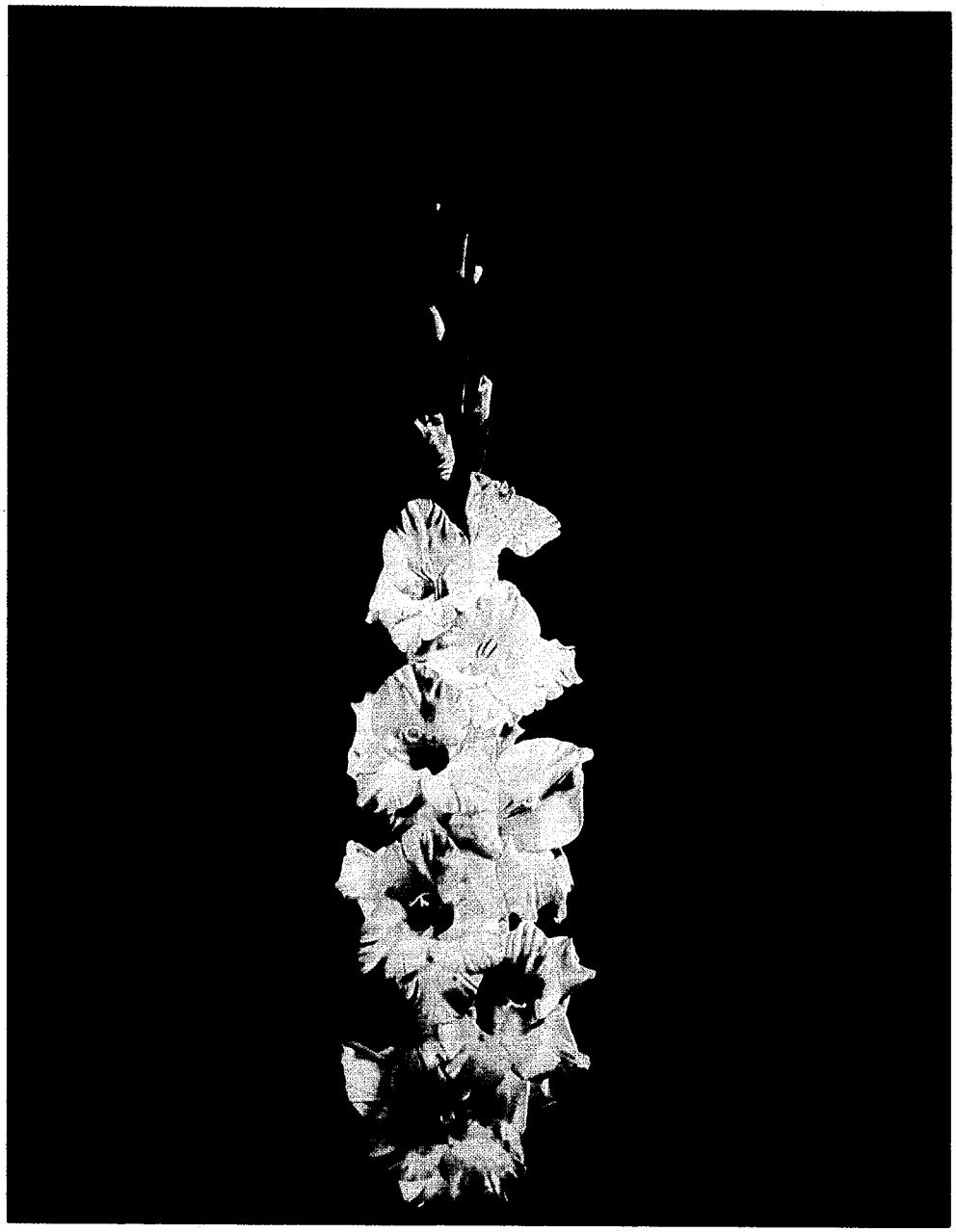
Inventor.
Carl Fischer
By: Robb & Robb
Attorneys.

United States Patent Office

Plant Pat. 2,253
Patented Apr. 16, 1963

2,253
GLADIOLUS PLANT

Carl Fischer, St. Charles, Minn., assignor to Imperial Flowers Limited, Leamington, Ontario, Canada, a corporation of Ontario Filed May 9, 1962, Ser. No. 193,639
1 Claim. (Cl. 47—60)

The present invention relates to a new and distinct variety of gladiolus plant which was originated by me by crossing the variety known as "Prospector" (unpatented) with an unnamed and unpatented seedling of unidentified parentage, said cross having been made by me by manual cross pollination as performed in my outdoor breeding fields at St. Charles, Minnesota.

The primary objective of this breeding was to produce a new and superior variety of gladiolus having yellow flowers. This objective was fully achieved, along with other desirable features, as evidenced by the following unique combination of characteristics which are outstanding in the new variety and which distinguish it from its parents, as well as from all other varieties of which I am aware:

(1) Good general vigor;
(2) Robust growth;
(3) Straight and stiff stems;
(4) An attractive ruffled flower form; and
(5) A distinctive and attractive Aureolin general color tonality of the flowers.

My new variety resembles the variety known as "Golden Sunshine" (unpatented) more than any other, but differs principally therefrom by having straighter and stiffer flower stems, as well as a more ruffled form of the flowers and greater temperature tolerance.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely rugged; excellent propagator; blossom spike attains height ranging from about 56 inches to 60 inches.

Blooming habit: Rather late bloomer in the northern latitudes of the United States; comes into bloom from large bulbs in about 90 days.

Stems: Straight; willowy.
*Diameter at base.*—½ inch.
*Color (just above the bulb).*—Rosy-purple.

Foliage: Extremely healthy; broad leaves averaging 2 inches wide; leaves attain height of about 42 inches; upright and fan-shaped. Color—green.

Disease resistance: Unusually resistant to Fusarium yellows, Sclerotina dry rot and Septoria leaf spot, as determined by comparison with other varieties grown in my fields near St. Charles, Minnesota, in irrigated black loam soil.

Corms (bulbs): Round and quite high-crowned; thick and heavy husk having purplish cast near the stem; deep basal scar. Color of flesh—Indian Yellow, Plate 6/2.

*Flower*

Spike: Tall; heavy; bears from 18 to 20 buds, with 6 to 8 buds opening at once and 5 or 6 buds showing color; flower head averages about 26 inches long.

Bud:
*Size.*—About 2½ inches long when opening.
*Opening.*—5 or 6 buds show color at one time; opens well from tight bud.

Flower:
*Arrangement.*—Florets are semiformally arranged (nearly in a double row) on the stem and usually all face forward.
*Size.*—Individual florets average about 4½ inches in diameter, with upper blooms being progressively smaller.
*Form.*—Florets are extremely round and heavily ruffled.
*Keeping qualities.*—Good.

Petals:
*Shape.*—Very round; ruffled; recurved; with some needle-pointing.
*Size.*—Outer petals—range from about 2¼ inches to 2½ inches in width. Lip petal—ranges from about 1½ inches to 1¾ inches in width.
*Aspect.*—Extremely heavy substance; broad and smooth surface.
*Fragrance.*—None.
*Color.*—Aureolin, Plate 3/2, shading somewhat deeper in the throat to Aureolin, Plate 3/1; practically uniformly colored.

*Reproductive Organs*

Stamens: Color—purple.
Pistil: Color—yellow.

I claim:

A new and distinct variety of gladiolus plant, substantially as herein shown and described, characterized particularly as to novelty by the unique combination of good general vigor, robust growth, straight and stiff stems, an attractive ruffled flower form, and a distinctive and attractive Aureolin general color tonality of the individual florets which are somewhat deeper in shade in the throat.

No references cited.